(12) United States Patent
Sun et al.

(10) Patent No.: US 11,948,247 B2
(45) Date of Patent: Apr. 2, 2024

(54) CAMERA-BASED TRANSCRANIAL MAGNETIC STIMULATION DIAGNOSIS AND TREATMENT HEAD MODELING SYSTEM

(71) Applicant: WUHAN ZNION TECHNOLOGY CO., LTD, Hubei (CN)

(72) Inventors: Cong Sun, Hubei (CN); Bo Wang, Hubei (CN); Shengan Cai, Hubei (CN)

(73) Assignee: WUHAN ZNION TECHNOLOGY CO., LTD (CN)

( * ) Notice: Subject to any disclaimer, the term of this patent is extended or adjusted under 35 U.S.C. 154(b) by 457 days.

(21) Appl. No.: 17/283,539

(22) PCT Filed: Feb. 26, 2019

(86) PCT No.: PCT/CN2019/076101
§ 371 (c)(1),
(2) Date: Apr. 7, 2021

(87) PCT Pub. No.: WO2020/172780
PCT Pub. Date: Sep. 3, 2020

(65) Prior Publication Data
US 2021/0390771 A1 Dec. 16, 2021

(51) Int. Cl.
*G06T 17/00* (2006.01)
*A61B 5/00* (2006.01)
(Continued)

(52) U.S. Cl.
CPC ............ *G06T 17/00* (2013.01); *A61B 5/0064* (2013.01); *A61B 5/0077* (2013.01); *G06T 19/20* (2013.01); *H04N 13/239* (2018.05); *A61N 2/006* (2013.01); *A61N 2/02* (2013.01); *G06T 2200/08* (2013.01); *G06T 2210/41* (2013.01);
(Continued)

(58) Field of Classification Search
CPC ..... G06T 17/00; G06T 19/20; G06T 2200/08; G06T 2210/41; A61B 5/0064; A61B 5/0077
See application file for complete search history.

(56) References Cited

U.S. PATENT DOCUMENTS

2015/0227680 A1* 8/2015 Mainkar ................. G06T 17/00
703/11

OTHER PUBLICATIONS

M. Martin, F. Van De Camp and R. Stiefelhagen, "Real Time Head Model Creation and Head Pose Estimation on Consumer Depth Cameras," 2014 2nd International Conference on 3D Vision, Tokyo, Japan, 2014, pp. 641-648, doi: 10.1109/3DV.2014.54. (Year: 2014).*

* cited by examiner

*Primary Examiner* — Colin T. Sakamoto
*Assistant Examiner* — Tommy T Ly

(57) ABSTRACT

A camera-based Transcranial Magnetic Stimulation (TMS) diagnosis and treatment head modeling system is provided and includes a 3D scanner, a positioning cap, and a smart terminal, where the 3D scanner and the smart terminal are electrically connected. A modeling method for the head modeling system includes: acquiring 3D image data of the head of a patient by a camera from different directions, and integrating the image data to obtain complete 3D image data; and then mapping, in combination with MNI brain space coordinates, a skull model obtained by brain 3D scanning in an MNI space to 3D head model data of the patient to obtain a head model highly matching the real head of the patient.

7 Claims, 6 Drawing Sheets

(51) Int. Cl.
- G06T 19/20 (2011.01)
- G06V 40/16 (2022.01)
- H04N 13/239 (2018.01)
- A61N 2/00 (2006.01)
- A61N 2/02 (2006.01)

(52) U.S. Cl.
CPC .. *G06T 2210/56* (2013.01); *G06T 2219/2016* (2013.01); *G06V 40/171* (2022.01)

CAMERA-BASED TRANSCRANIAL MAGNETIC STIMULATION DIAGNOSIS AND TREATMENT HEAD MODELING SYSTEM

FIELD

The present invention relates to the technical field of transcranial magnetic stimulation medical treatment, in particular, to a camera-based transcranial magnetic stimulation diagnosis and treatment head modeling system.

BACKGROUND

According to statistics from the Mental Health Center of the Chinese Center for Disease Control and Prevention, the total number of patients with mental illness in China has exceeded 100 million at present, but the public's awareness of mental illness is less than 50%, and the consultation rate is even lower. At present, about 20% of the patients with mental illness receive timely treatment, and 80% of the patients with mental illness are not treated in time, or even the most basic treatment. The number of patients with severe mental illness is as high as 16 million. According to the latest statistical data from the IMS Health, the global consumption of drugs for mental illness have exceeded 36 billion U.S. dollars, accounting for 5% of the total drug sales. However, as far as China is concerned, the current mental illness drug market is still relatively small, accounting for about 1.5% of the total hospital sales. There are already more than 600 psychiatric hospitals in China, but compared with the increasing incidence of mental illness, there is still a great gap to the needs of patients with mental illness in quantity and quality. There are still a large number of patients with mental illness who cannot get professional, systematic, and effective treatment.

Transcranial Magnetic Stimulation (TMS) is a technique to generate an electric current in the local cerebral cortex by a pulsed magnetic field to temporarily activate or inhibit the cortex. In the current field of medical devices, the operation of a TMS treatment device is to control a TMS coil by manual operation or by fixing same using a support to treat a patient. Manual operation is very inconvenient, and the coil needs to be held by hand for a long time or needs to be fixed at a specific angle by a support. The patient does not have good experience, because the patient needs to sit and keep a posture and dare not move. There are also some automated operation devices that use a smart terminal to control a mechanical arm to clamp the TMS coil to perform magnetic stimulation treatment on the head of a patient. The first step in treating a patient by an automated operation device is to construct a head model of the patient, match the head model of the patient with the real head of the patient in a 3D space coordinate system, and then plan the movement path of the mechanical arm in the space coordinate system, where the most important step is to construct the head model of the patient. Once the constructed head model does not match the real head of the patient, subsequent treatment cannot be carried out. Most of the existing head modeling methods are to directly construct a head model through software (such as YAMA). However, a head model directly constructed by software is general and cannot match the heads of all patients, which reduces the matching accuracy, results in inaccurate positioning of a magnetic stimulation point on the head of a patient, and greatly reduces the magnetic stimulation treatment effect.

Another head modeling method (such as "modeling methods and devices for an anisotropic electrical conductivity head model combined with cortical excitability" published on Dec. 28, 2018 in a Chinese patent with the publication number CN109102894A) is to construct an anisotropic electrical conductivity head model based on MRI and DTI images, then obtain an individual cortical excitability comprehensive index through an array magnetic stimulation point TMS experiment, and finally construct, according to the anisotropic electrical conductivity head model and the individual cortical excitability comprehensive index, an anisotropic electrical conductivity head model including cortical excitability. This method is complicated and high in cost.

SUMMARY

The purpose of the present invention is to provide a camera-based Transcranial Magnetic Stimulation (TMS) diagnosis and treatment head modeling system in view of the problem existing in the prior art. 3D image data of the head of a patient is acquired by a 3D camera from different directions, and the image data are integrated to obtain complete 3D image data matching the real head of the patient. The modeling system in the present invention has low cost and high automation, and does not require excessive manual operations. Moreover, a constructed head highly fits the head of a patient, thereby effectively improving the accuracy of subsequent positioning of a magnetic stimulation point for magnetic stimulation, and improving the treatment effect. The head modeling method in the present invention solves the problem in the prior art that the magnetic stimulation treatment effect is reduced due to mismatch between a head model and the head of a patient caused by the use of software to construct the head model, and also solves the problems in the prior art of high cost and great operation difficulty caused by the construction of an anisotropic electrical conductivity head model including cortical excitability based on an anisotropic electrical conductivity head model and an individual cortical excitability comprehensive index.

In order to achieve the purpose above, the present invention adopts the following technical solutions.

A camera-based TMS diagnosis and treatment head modeling system, including a 3D scanner, a positioning cap, and a smart terminal, where the 3D scanner and the smart terminal are electrically connected; and a modeling method for the head modeling system includes the following steps:

S1, making a patient wear the positioning cap, starting the smart terminal, acquiring, by the 3D scanner, 3D image data of the head of the patient from different directions, and sending the acquired 3D image data to the smart terminal;

S2, integrating, by the smart terminal, the 3D image data acquired by the 3D scanner from different directions to obtain a complete 3D point cloud image of the head of the patient, and then obtaining complete 3D head model data of the head of the patient through sampling, smoothing, and plane fitting processing; and S3, mapping, by using the 3D head model data in combination with MNI brain space coordinates, 3D skull data in an MNI space to the 3D head model data of the patient to obtain a 3D head model of the patient.

Specifically, the 3D scanner includes one 3D camera and one rotating support, the 3D camera is installed on the rotating support, the rotating support is driven to rotate by a motor, and the motor is electrically connected to the smart terminal; and when the 3D image data of the head of the patient is acquired, the smart terminal controls the motor to drive the rotating support to rotate at a uniform speed, so that the 3D camera moves circumferentially around the head of the patient at a uniform speed and acquires the 3D image data of the head of the patient from different directions.

Specifically, the 3D scanner may also include several 3D cameras and one fixing support, and the several 3D cameras are all installed on the fixing support; and when the 3D image data of the head of the patient is acquired, the smart terminal controls the several 3D cameras to simultaneously acquire the 3D image data of the head of the patient from different directions.

Further, the image data captured by the 3D camera includes a color image, a depth image, and a 3D point cloud image. The 3D camera is disposed above the face of the patient and can fully incorporate the face of the patient into a photographing range.

Specifically, in step S1, the positioning cap is a white head cover made of an elastic material, and is configured to cover hair of the patient. Because the 3D scanner cannot scan black hair without heat, it is necessary to cover the hair with the white head cover to expose the five sense organs and forehead of the patient, and to mark facial feature points (the eyebrow center, the nose tip, etc.). The positioning cap is elastic, suitable for a wide range of people, and easy to wear. The positioning cap is provided with several Mark points to facilitate image data acquisition by a 3D camera.

Specifically, in step S2, a method for integrating the 3D image data acquired from different directions includes: calculating, by identifying facial feature points in images acquired from different directions, a matching relationship between the images, then obtaining, through a 3D point cloud ICP algorithm, a spatial position relationship between point cloud images acquired from different directions, and finally, performing rotation and translation operations on all point cloud image data according to the matching relationship and the spatial position relationship to obtain the complete 3D point cloud image of the head of the patient.

Specifically, in step S3, the mapping method includes: selecting four points NZ, CZ, AL, and AR on the head of the patient and comparing same with the four points on a skull model to obtain a skull model conversion matrix, and then multiplying points in an MNI space by the conversion matrix to obtain coordinate points of a head model of the patient, where NZ stands for the nasal root, AL stands for the left ear, AR stands for the right ear, and CZ stands for a point where a line connecting the nasal root and the occipital protuberance intersects a line connecting the left and right ears.

The present invention further provides a camera-based TMS diagnosis and treatment detection system, for use in positioning a spatial position of a magnetic stimulation point on the head of the patient based on the 3D head model constructed above. The detection system includes: a 3D camera, a horizontal bed, a headrest, and a smart terminal. The 3D camera is configured to capture a facial image of the patient, and the facial image of the patient is matched with the 3D head model by the smart terminal to obtain magnetic stimulation point positioning information for TMS diagnosis and treatment. A detection method for the detection system includes the following steps:

S1, making a patient lie on the horizontal bed, and adjusting a longitudinal position of the horizontal bed so that the horizontal bed reaches a treatment position;

S2, before treatment is started, capturing image data of the head of the patient by the 3D camera, and performing head modeling by the smart terminal to construct a 3D head model of the head of the patient; and S3, when the treatment is started, capturing a real-time facial image of the patient by the 3D camera, and performing pose matching by the smart terminal for position matching of the real-time facial image with the constructed 3D head model, further including: marking facial feature points for matching in the 3D head model; automatically identifying facial feature points in the real-time facial image of the patient by the 3D camera; performing affine transformation through feature point matching to obtain a conversion matrix, and calculating a conversion relationship between the real-time facial image of the patient and the constructed 3D head model; calculating a position of the 3D head model in space; and calculating position coordinates of a magnetic stimulation point on the 3D head model in space.

Preferably, the detection method further includes: in the process of performing magnetic stimulation treatment on the head of the patient, performing, by the smart terminal, follow-up positioning on the head of the patient by means of the 3D camera; during the treatment, recording position information of the magnetic stimulation point on the head of the patient each time positioning is completed, and if at a next moment, a distance between positions of the magnetic stimulation point at a current time and a previous time exceeds 5 mm due to movement of the head of the patient, starting follow-up positioning; and if the distance does not exceed 5 mm, not starting follow-up positioning.

The present invention further provides a camera-based TMS diagnosis and treatment navigation system, for use in planning a movement path for a mechanical arm after detecting spatial coordinates of a magnetic stimulation point on the head of a patient. The navigation system includes: a 3D camera, a horizontal bed, a headrest, a mechanical arm, a TMS coil, and a smart terminal, where the mechanical arm and the TMS coil are separately electrically connected to the smart terminal. A navigation method for the navigation system includes the following steps:

S1, making a patient lie on the horizontal bed, and adjusting a longitudinal position of the horizontal bed so that the horizontal bed reaches a treatment position;

S2, modeling the head of the patient by using the 3D camera and the smart terminal;

S3, matching a position of a head model of the patient with an actual position of the head of the patient by the 3D camera and the smart terminal, and determining a spatial position of a magnetic stimulation point to be magnetically stimulated on the head model of the patient;

S4, modeling the mechanical arm, the TMS coil, and the 3D camera by the smart terminal; and S5, placing device models constructed in step S4 and the head model of the patient constructed in step S2 in a same spatial coordinate system; then calculating, by the smart terminal, an optimal path for a TMS coil model to reach the magnetic stimulation point to be magnetically stimulated on the head model, and then automatically navigating movement of the mechanical arm according to the optimal path by the smart terminal, to finally move the TMS coil to the magnetic stimulation point to be magnetically stimulated on the head of the patient for treatment.

Further, in step S3, a method for matching the position of the head model of the patient with the actual position of the head of the patient includes the following steps:

S31, marking facial feature points for alignment on the head model of the patient;

S32, identifying facial feature points of the patient by the 3D camera;

S33, performing matching calculation on the facial feature points marked in step S31 and the facial feature points identified in step S32 to obtain a rotation and translation relationship between the head of the patient and the head model of the patient; and S34, performing rotation and translation operations on the head model of the patient according to the rotation and translation relationship, so that the position of the head model of the patient is match with the actual position of the head of the patient.

Further, in step S4, after modeling the mechanical arm, the TMS coil, and the 3D camera, spatial positions of a mechanical arm model, the TMS coil model, and a 3D camera model need to be matched with actual spatial positions of the mechanical arm, the TMS coil, and the 3D camera, respectively. A specific matching method includes:

S41, marking feature points for alignment on the mechanical arm model;

S42, identifying feature points of the mechanical arm when in an initial position by the 3D camera;

S43, performing matching calculation on the feature points marked in step S41 and the feature points identified in step S42 to obtain a rotation and translation relationship between the mechanical arm model and the mechanical arm;

S44, obtaining rotation and translation relationships respectively between the 3D camera model and the 3D camera and between the TMS coil model and the TMS coil according to the principle that the relative positions of the 3D camera, the TMS coil, and the mechanical arm are fixed when the mechanical arm is in the initial position; and S45, performing rotation and translation operations on the mechanical arm model, the TMS coil model, and the 3D camera model according to the rotation and translation relationships in step S43 and step S44, so that spatial positions of the mechanical arm model, the TMS coil model, and the 3D camera model are respectively matched with actual spatial positions of the mechanical arm, the TMS coil, and the 3D camera.

Preferably, the navigation method further includes a follow-up positioning step. The follow-up positioning step includes: fine-tuning the spatial pose of the head model of the patient by the smart terminal, so that the spatial pose of the head model of the patient is matched with the current actual spatial pose of the head of the patient, then repositioning a latest magnetic stimulation point on the head model, finally re-planning a movement path for the mechanical arm, and moving the TMS coil to the latest magnetic stimulation point for treatment.

Compared with the prior art, the beneficial effects of the present invention are as follows: (1) according to the present invention, 3D image data of the head of a patient is acquired by a camera from different directions, and the image data is integrated to obtain complete 3D image data; and then in combination with MNI brain space coordinates, 3D skull data in an MNI space is mapped to 3D head model data of the patient to obtain a head model highly matching the real head of the patient. Thus, the accuracy of subsequent positioning of a magnetic stimulation point for magnetic stimulation on the head of the patient is improved, and the TMS magnetic stimulation treatment effect is greatly improved. (2) In the present invention, a 3D head model of a patient may be obtained by only acquiring 3D data of the head of the patient by a 3D camera and processing the acquired data through a smart terminal. The cost is low, the operation is simple, and the degree of automation is high.

Figure 1:
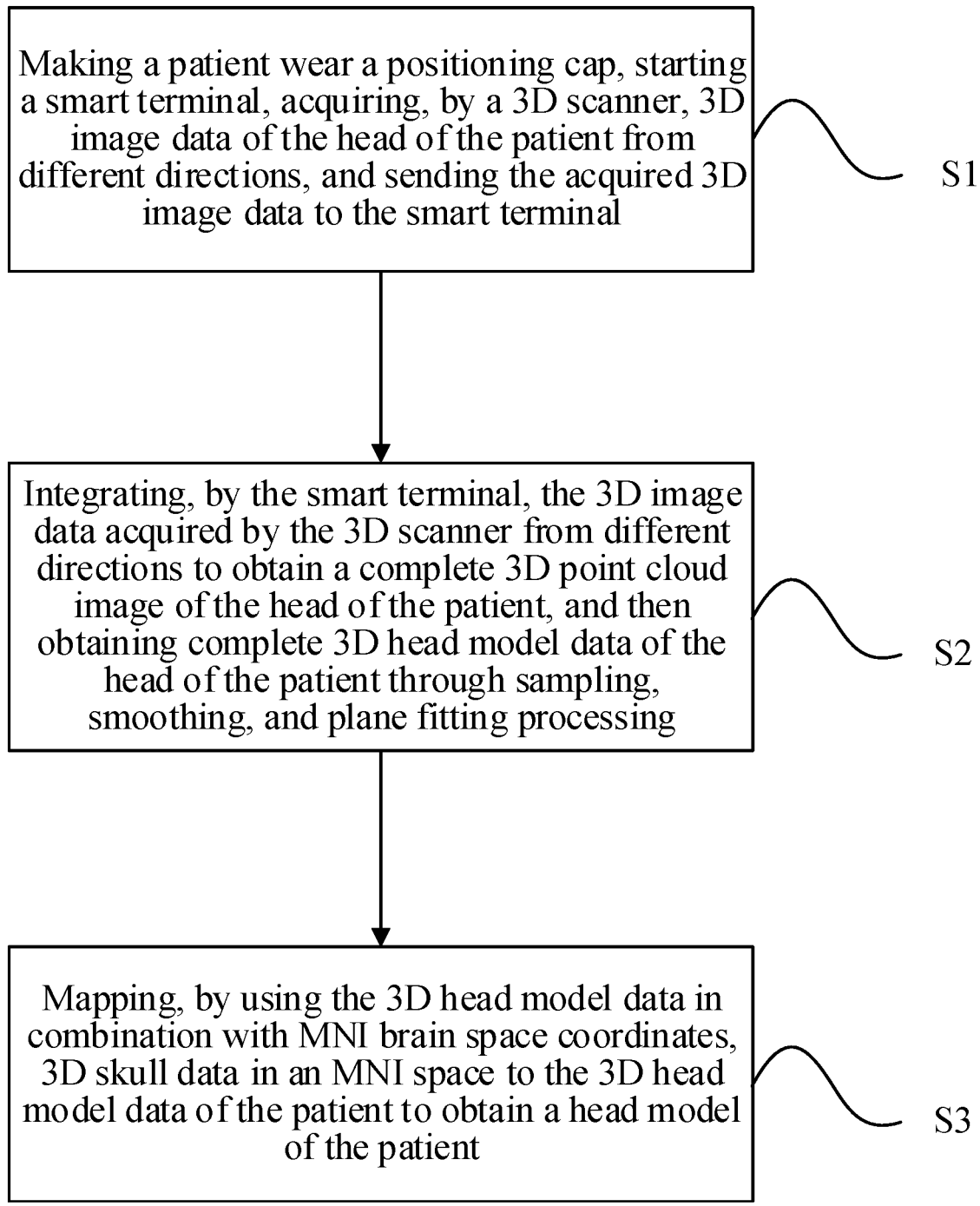
FIG. 1 is a flowchart of a modeling method for a camera-based Transcranial Magnetic Stimulation (TMS) diagnosis and treatment head modeling system according to the present invention.

In the drawings: 1. horizontal bed; 2. headrest; 3. 3D camera; 4. mechanical arm; 5 TMS coil; 6. rotating support; 7. motor; 8. 3D scanner; 9. smart terminal; 10. seat; 11. camera installation position; 12. fixing support.

DETAILED DESCRIPTION

The technical solutions of the present invention are clearly and fully described below with reference to the accompanying drawings in the present invention. Apparently, the described embodiments are merely some of the embodiments of the present invention, but not all the embodiments. Based on the embodiments of the present invention, all other embodiments that may be implemented by persons of ordinary skill in the art without involving an inventive effort shall fall within the scope of protection of the present invention.

In the present invention, the terms "install", "link", and "connect" should be understood in a broad sense, and may be, for example, a mechanical connection or an electrical connection, or a connection between two components, or a direct link, or an indirect link using an intermediary. For persons of ordinary skill in the art, the specific meanings of the above terms may be understood according to specific circumstances.

As an embodiment of the present invention, this embodiment provides a camera-based Transcranial Magnetic Stimulation (TMS) diagnosis and treatment head modeling system, including a 3D scanner, a positioning cap, a seat, and a smart terminal, where the 3D scanner and the smart terminal are electrically connected, and the smart terminal may be a computer.

As shown in FIG. 1, a modeling method for the head modeling system includes the following steps.

At S1, a patient sits on the seat and wears the positioning cap, the smart terminal is started, and the 3D scanner acquires 3D image data of the head of a patient from different directions, and sends the acquired 3D image data to the smart terminal.

At S2, the smart terminal integrates the 3D image data acquired by the 3D scanner from different directions to obtain a complete 3D point cloud image of the head of the patient, and then obtains complete 3D head model data of the head of the patient through sampling, smoothing, and plane fitting processing.

At S3, 3D skull data in an MNI space is mapped to the 3D head model data of the patient by using the 3D head model data in combination with MNI brain space coordinates commonly used in medicine, to obtain a 3D head model of the patient.

Figure 2:
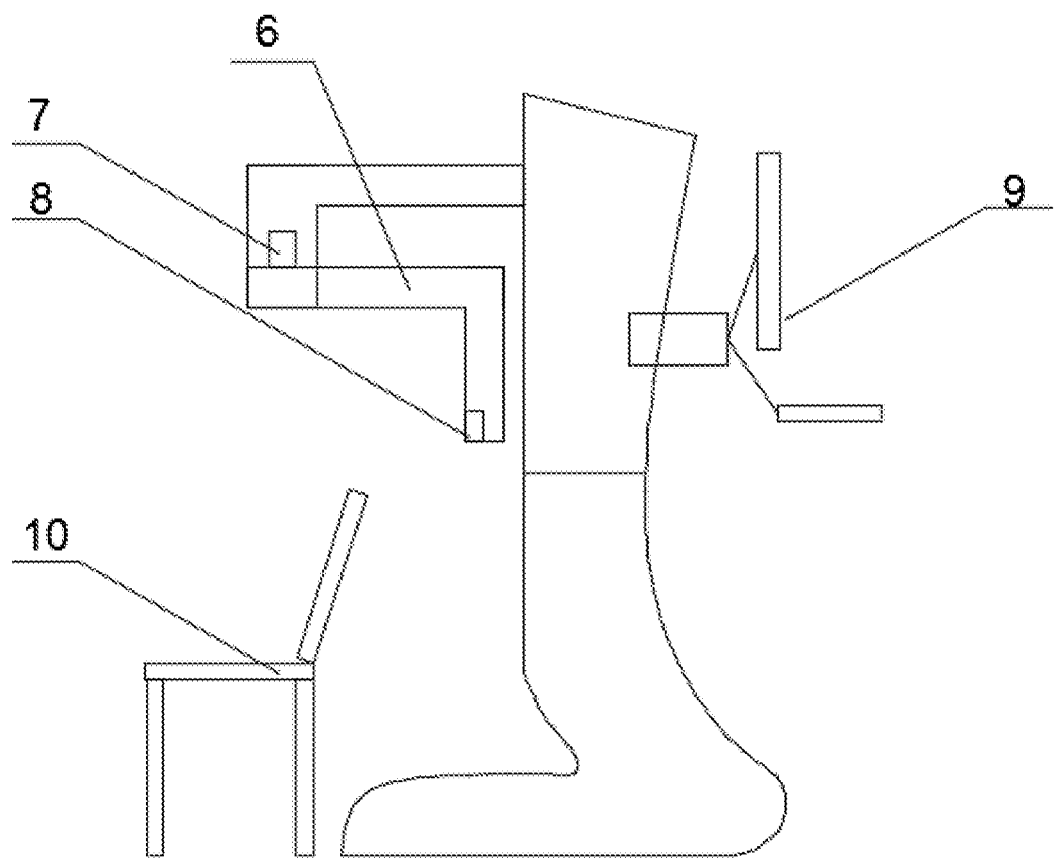
FIG. 2 is a schematic structural diagram of a camera-based TMS diagnosis and treatment head modeling system according to an embodiment of the present invention.

Specifically, as shown in FIG. 2, the 3D scanner includes one 3D camera and one rotating support, the 3D camera is installed on the rotating support, the rotating support is driven to rotate by a motor, and the motor is electrically connected to the smart terminal. When the 3D image data of the head of the patient is acquired, the smart terminal controls the motor to drive the rotating support to rotate at a uniform speed, so that the 3D camera moves circumferentially around the head of the patient at a uniform speed and acquires the 3D image data of the head of the patient from different directions.

Specifically, in step S1, the positioning cap is a white head cover made of an elastic material, and is configured to cover hair of the patient. Because the 3D scanner cannot scan black hair without heat, it is necessary to cover the hair with the white head cover to expose the five sense organs and forehead of the patient, and to mark feature points (the eyebrow center, the nose tip, etc.). The positioning cap is elastic, suitable for a wide range of people, and easy to wear. The positioning cap is provided with several Mark points to facilitate image data acquisition by a 3D camera.

Specifically, in step S2, a method for integrating the 3D image data acquired from different directions includes: calculating, by identifying feature points in images acquired from different directions, a matching relationship between the images, then obtaining, through a 3D point cloud ICP algorithm, a spatial position relationship between point cloud images acquired from different directions, and finally, performing rotation and translation operations on all point cloud image data according to the matching relationship and the spatial position relationship to obtain the complete 3D point cloud image of the head of the patient.

Further, modeling a head needs to acquire 3D scan data of the head of a patient by a 3D camera. Each time the 3D camera performs photographing, a color image, a depth image, and a 3D point cloud image are generated. The three images are generated at the same time, and thus, points on the images have a fixed corresponding relationship. The corresponding relationship is known and is obtained through calibration of the camera. 3D scanning is to capture a series of images around the head of a patient, and then stitch the images into a complete image. Image stitching involves finding the same parts of two images and matching same. No 3D point cloud for hair can be obtained in a 3D camera, but 3D data of the skull (without hair) is needed in a medical treatment head model. Therefore, a patient needs to wear a specific positioning cap during scanning for a head model. In order to make the matching more accurate, some mark points are usually provided on the cap. 3D scanning ultimately needs to stitch 3D point clouds. The rotation and translation relationship between point clouds of all images is needed during stitching. The stitching of point clouds mainly relies on an ICP algorithm. The ICP algorithm sometimes fails, so rough matching is required first.

Further, stitching of point clouds includes the follow steps.

At S21, "key points" are first calculated in a color image through cv::FeatureDetector and cv::DescriptorExtractor in OpenCV, "descriptors" of pixels around the key points are calculated, then the above descriptors are matched using cv::DMatch, and then a SolvePnPRansac function in OpenCV is called to solve PnP to obtain displacement and rotation information of two images.

At S22, point cloud data of the two images are calculated by using the displacement and rotation information calculated above as a result of initial coarse matching of the ICP algorithm to obtain more accurate displacement and rotation data.

At S23, a displacement and rotation matrix is obtained using the above displacement and rotation data, all points in a previous point cloud image are rotated and translated, and a new point cloud calculated is added to a current point cloud image to obtain a larger point cloud, so that integration of the two point clouds is completed.

At S24, steps S21 to S23 are repeated, all point cloud images are integrated into a larger point cloud image, then filtering and smoothing processing is performed on the point cloud image, sampling is performed to reduce the number of points, and fitting is performed to obtain 3D curved surface data, so as to obtain complete 3D data of the head of the patient.

Specifically, in step S3, the mapping method includes: selecting four points NZ, CZ, AL, and AR on the head of the patient and comparing same with the four points on a skull model to obtain a skull model conversion matrix, and then multiplying points in an MNI space by the conversion matrix to obtain coordinate points of a head model of the patient, where NZ stands for the nasal root, AL stands for the left ear, AR stands for the right ear, and CZ stands for a point where a line connecting the nasal root and the occipital protuberance intersects a line connecting the left and right ears.

Figure 3:
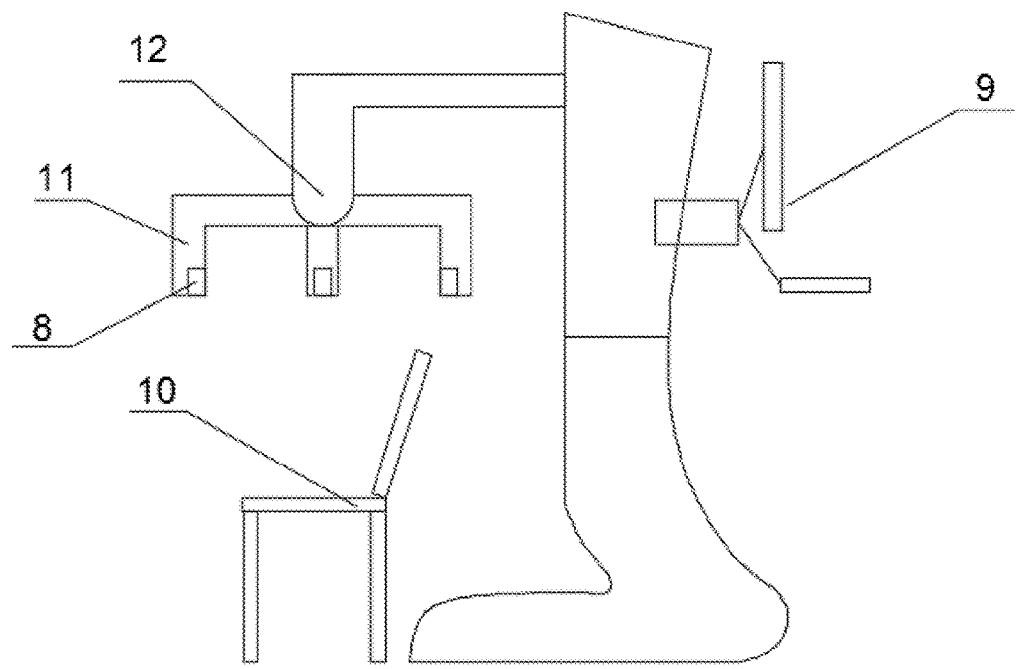
FIG. 3 is a schematic structural diagram of a camera-based TMS diagnosis and treatment head modeling system according to another embodiment of the present invention.

As another embodiment of the present invention, as shown in FIG. 3, this embodiment provides a camera-based TMS diagnosis and treatment head modeling system. A 3D scanner in this embodiment includes three 3D cameras and one fixing support.

Figure 4:
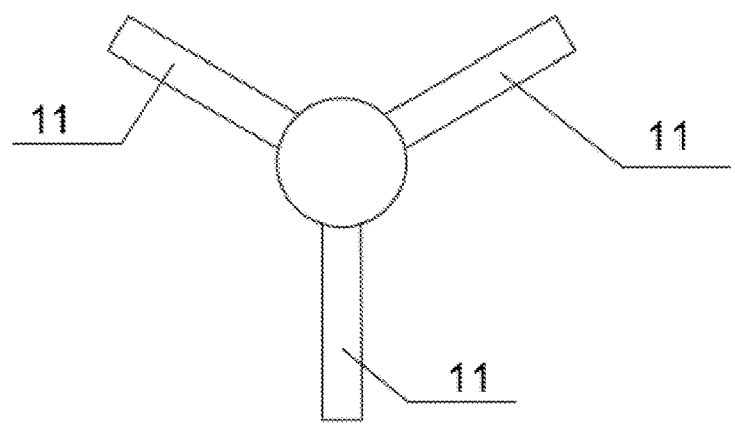
FIG. 4 is a schematic diagram of arrangement of a camera installation position according to another embodiment of the present invention.

Specifically, as shown in FIG. 4, the fixing support is provided with three camera installation positions, the included angle between two adjacent camera installation positions is 120 degrees, and the three 3D cameras are respectively installed on the three camera installation positions.

When 3D image data of the head of a patient is acquired, the three 3D cameras are controlled by a smart terminal to simultaneously acquire the 3D image data of the head of the patient in three directions.

In this embodiment, 3D image data of the head of a patient is simultaneously acquired through three 3D cameras, and the acquired data is sent to a smart terminal for head modeling, thus achieving good real-time property.

Figure 5:
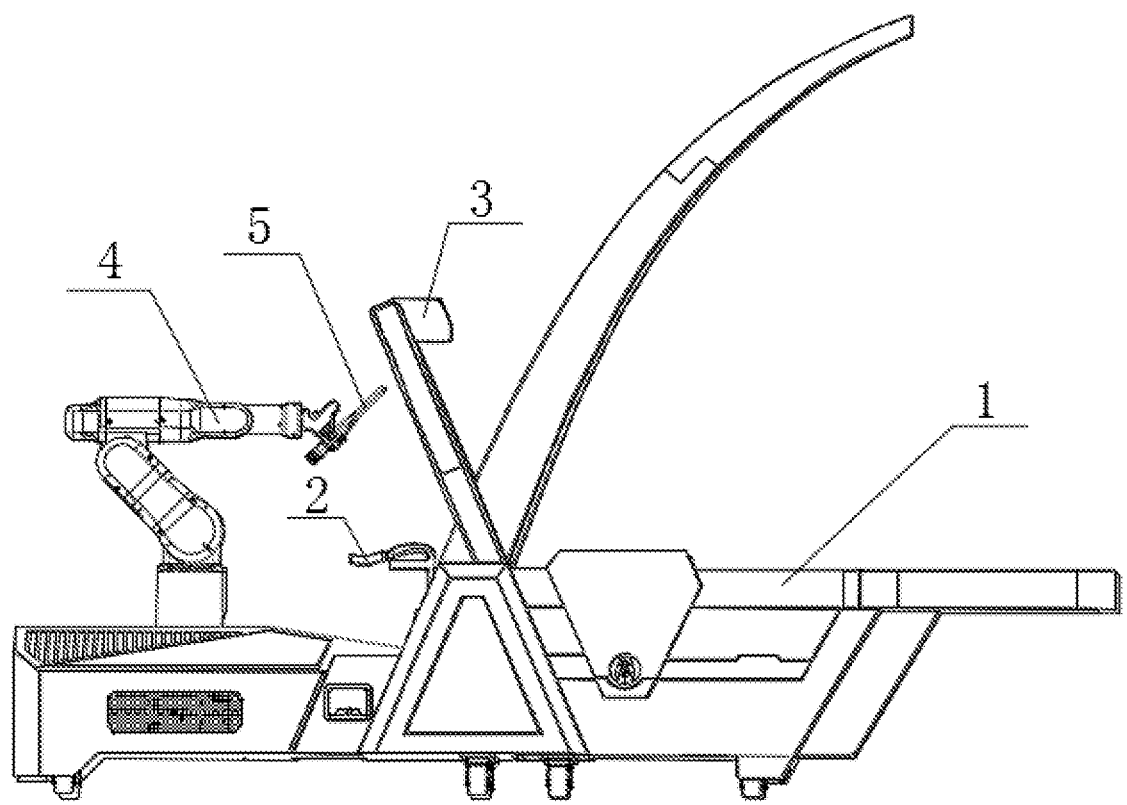
FIG. 5 is a schematic structural diagram of a camera-based TMS diagnosis and treatment detection system according to still another embodiment of the present invention.

As still another embodiment of the present invention, as shown in FIG. 5, a camera-based TMS diagnosis and treatment detection system is provided, for use in performing magnetic stimulation treatment on the head of the patient based on the 3D head model constructed above. The detection system includes: a 3D camera, a horizontal bed, a headrest, and a smart terminal. The 3D camera is configured to capture a facial image of the patient, and the facial image of the patient is matched with the 3D head model by the smart terminal to obtain magnetic stimulation point positioning information for TMS diagnosis and treatment. The smart terminal may be a computer, a laptop, a tablet, etc.

The horizontal bed is a horizontal translation platform, can be moved forwards and backwards, and is configured to adjust the relative positions of the head of the patient and the camera.

The headrest 2 mainly has a supporting function with a supporting site being the skull and also including the neck, has a function of limiting movement of a patient without causing discomfort to the patient, and cannot hinder magnetic stimulation of the head.

The 3D camera is configured to obtain head attitude data and real-time facial attitude data of a patient. Before treatment, the 3D camera is configured to obtain head attitude data of a patient, and the smart terminal is configured to perform 3D head modeling; after starting the treatment, the 3D camera is configured to obtain real-time facial data of the patient, and the smart terminal is configured to process the real-time facial data, and match a modeled 3D head model with a real-time facial image.

The 3D camera is further configured to obtain spatial poses of a mechanical arm and a TMS coil, so that the mechanical arm navigates the TMS coil to be clamped at the position of a magnetic stimulation point.

The mechanical arm is further configured to clamp the TMS coil to stimulate a magnetic stimulation point on the head of a patient for magnetic stimulation treatment.

Figure 6:
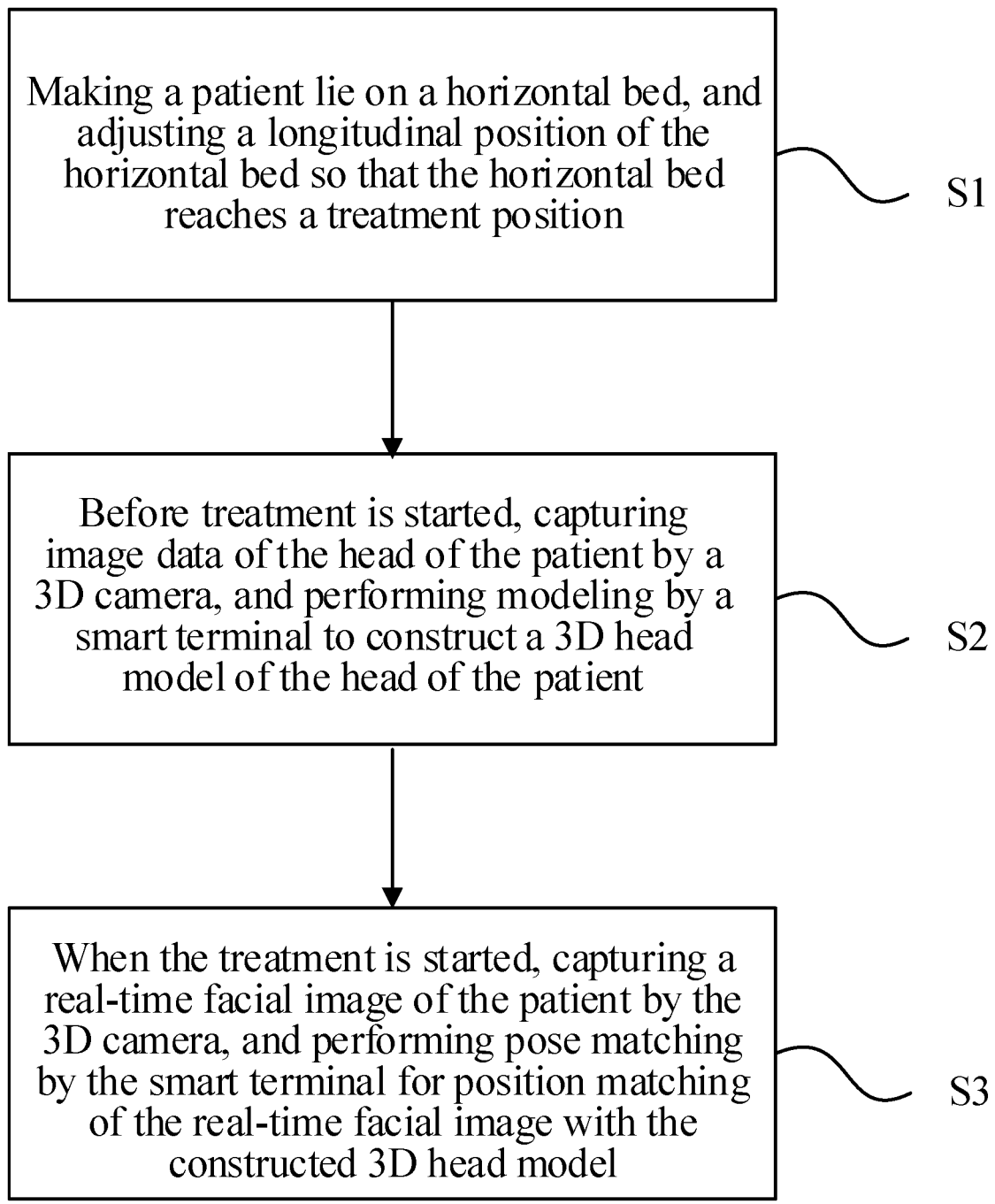
FIG. 6 is a flowchart of a detection method for a camera-based TMS diagnosis and treatment detection system according to still another embodiment of the present invention.

As shown in FIG. 6, a detection method for the detection system includes the following steps.

At S1, a patient lies on the horizontal bed, and a longitudinal position of the horizontal bed is adjusted so that the horizontal bed reaches a treatment position.

At S2, before treatment is started, image data of the head of the patient is captured by the 3D camera, and modeling is performed by the smart terminal to construct a 3D head model of the head of the patient.

At S3, when the treatment is started, a real-time facial image of the patient is captured by the 3D camera, and pose matching is performed by the smart terminal for position matching of the real-time facial image with the constructed 3D head model, further including: marking facial feature points for matching in the 3D head model, where the facial feature points are automatically identified by the camera during the modeling process; automatically identifying facial feature points in the real-time facial image of the patient by the 3D camera; performing affine transformation through feature point matching to obtain a conversion matrix, and calculating a conversion relationship between the real-time facial image of the patient and the constructed 3D head model; calculating a position of the 3D head model in a camera coordinate system; and calculating position coordinates of a magnetic stimulation point on the 3D head model in space.

Specifically, in step S3, the 3D image captured by the 3D camera in real time has only facial information of the patient but no head information, and thus, the head model constructed in S2 needs to be aligned in position with facial data captured in real time. Requirements of real-time detection cannot be satisfied due to a large calculation amount of an ICP algorithm. The position alignment method includes: first marking facial feature points (eye corners, the nose tip, etc.) for alignment in a head model, then automatically identifying the facial feature points in a real-time image, and calculating a conversion relationship between the real-time image and the head model through feature point matching, calculating a position of the head model in space, and then calculating position coordinates of a magnetic stimulation point on the head model in space.

The conversion relationship includes a rotation and translation relationship between the real-time facial image of the patient and the 3D head model in the camera coordinate system. The 3D head model is rotated and translated according to the rotation and translation relationship, and the 3D head model is matched onto the real-time facial image of the patient.

Preferably, the detection method further includes: in the process of performing magnetic stimulation treatment on the head of the patient, performing, by the smart terminal, follow-up positioning on the head of the patient by means of the 3D camera; during the treatment, recording position information of the magnetic stimulation point on the head of the patient each time positioning is completed, and if at a next moment, a distance between positions of the magnetic stimulation point at a current time and a previous time exceeds 5 mm due to movement of the head of the patient, starting follow-up positioning; and if the distance does not exceed 5 mm, not starting follow-up positioning.

Figure 7:
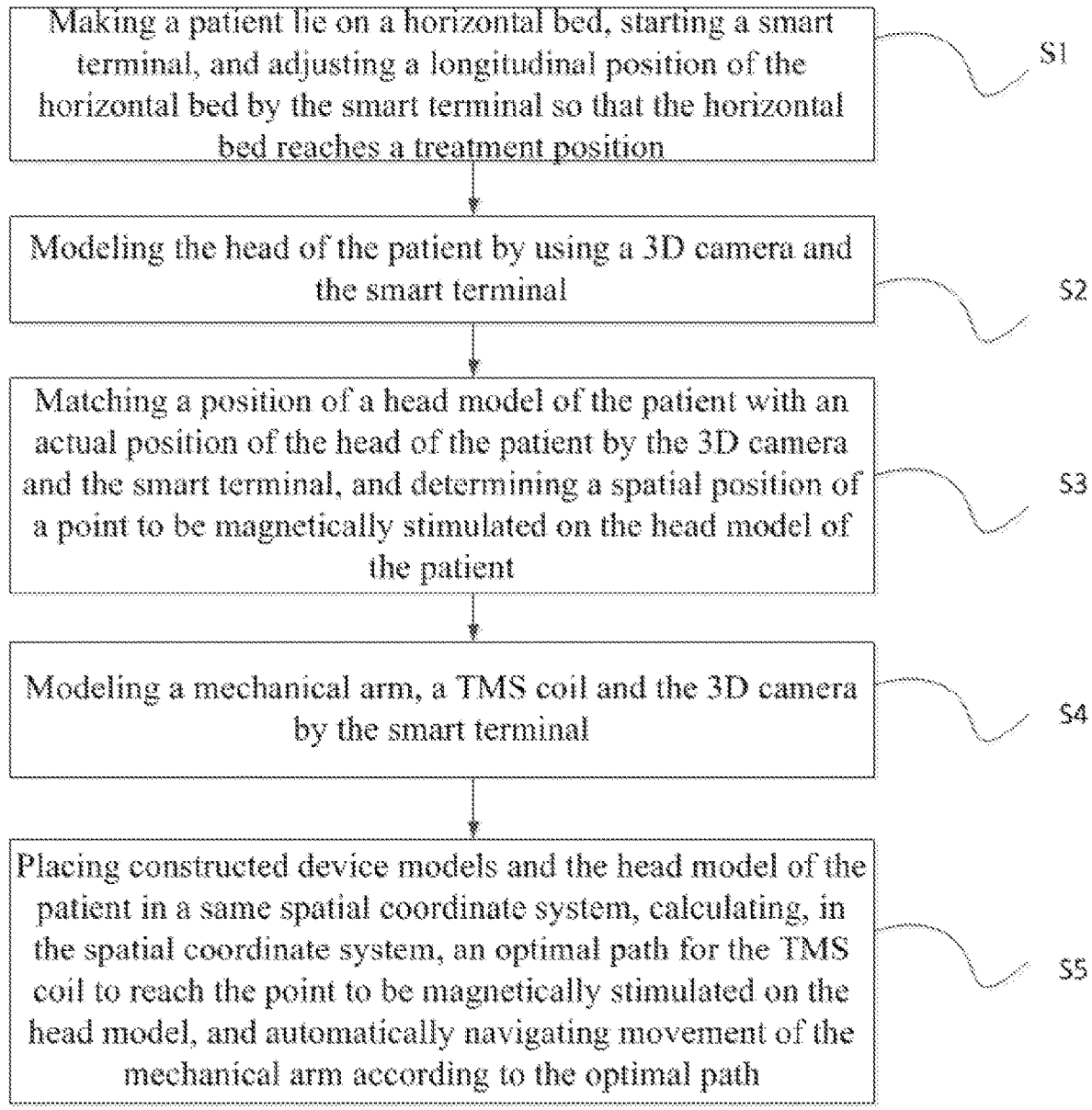
FIG. 7 is a flowchart of a navigation method for a camera-based TMS diagnosis and treatment navigation system according to still another embodiment of the present invention.

As still another embodiment of the present invention, as shown in FIG. 7, a camera-based TMS diagnosis and treatment navigation system is provided, for use in planning a movement path for a mechanical arm after detecting spatial coordinates of a magnetic stimulation point on the head of a patient. The navigation system includes: a 3D camera, a horizontal bed, a headrest, a mechanical arm, a TMS coil, and a smart terminal. The mechanical arm and the TMS coil are separately electrically connected to the smart terminal.

The 3D camera is configured to obtain spatial poses of the head of a patient and the mechanical arm, so as to navigate the mechanical arm.

The mechanical arm is configured to clamp the TMS coil to stimulate a magnetic stimulation point on the head of the patient for magnetic stimulation treatment.

As shown in FIG. 8, a navigation method for the navigation system includes the following steps.

At S1, a patient lies on the horizontal bed, and a longitudinal position of the horizontal bed is adjusted so that the horizontal bed reaches a treatment position.

At S2, the head of the patient is modeled by using the 3D camera and the smart terminal.

At S3, a position of a head model of the patient is matched with an actual position of the head of the patient by the 3D camera and the smart terminal, and a spatial position of a magnetic stimulation point to be magnetically stimulated on the head model of the patient is determined.

At S4, the mechanical arm, the TMS coil, and the 3D camera are modeled by the smart terminal.

At S5, device models constructed in step S4 and the head model of the patient constructed in step S2 are placed in a same spatial coordinate system; then an optimal path for a TMS coil model to reach the magnetic stimulation point to be magnetically stimulated on the head model is calculated by the smart terminal, and the smart terminal then automatically navigates movement of the mechanical arm according to the optimal path, to finally move the TMS coil to the magnetic stimulation point to be magnetically stimulated on the head of the patient for treatment.

Specifically, in step S3, the 3D image captured by the 3D camera in real time has only facial information of the patient but no head information, and thus, the head model constructed in S2 needs to be aligned in position with facial data captured in real time. Requirements of real-time detection cannot be satisfied due to a large calculation amount of an ICP algorithm. The position alignment method includes: first marking facial feature points (the eyebrow center, earlobes, eye corners, the nose tip, mouth corners, and the chin) for alignment in a head model, then automatically identifying the facial feature points in a real-time image, and calculating a conversion relationship between the real-time image and the head model through feature point matching, calculating a position of the head model in space, and then calculating position coordinates of a magnetic stimulation point on the head model in space. The specific steps are as follows.

At S31, facial feature points for alignment are marked on the head model of the patient.

At S32, facial feature points of the patient are identified by the 3D camera.

At S33, matching calculation is performed on the facial feature points marked in step S31 and the facial feature points identified in step S32 to obtain a rotation and translation relationship between the head of the patient and the head model of the patient.

At S34, rotation and translation operations are performed on the head model of the patient according to the rotation and translation relationship, so that the position of the head model of the patient is match with the actual position of the head of the patient.

Specifically, in step S4, SolidWorks software may be used to model the mechanical arm, the TMS coil, and the 3D camera, and after the modeling is completed, spatial positions of a mechanical arm model, the TMS coil model, and a 3D camera model need to be matched with actual spatial positions of the mechanical arm, the TMS coil, and the 3D camera, respectively. A specific matching method includes the following steps.

At S41, feature points for alignment are marked on the mechanical arm model.

At S42, feature points of the mechanical arm when in an initial position are identified by the 3D camera.

At S43, matching calculation is performed on the feature points marked in step S41 and the feature points identified in step S42 to obtain a rotation and translation relationship between the mechanical arm model and the mechanical arm.

At S44, rotation and translation relationships respectively between the 3D camera model and the 3D camera and between the TMS coil model and the TMS coil are obtained according to the principle that the relative positions of the 3D camera, the TMS coil, and the mechanical arm are fixed when the mechanical arm is in the initial position.

At S45, rotation and translation operations are performed on the mechanical arm model, the TMS coil model, and the 3D camera model according to the rotation and translation relationships in step S43 and step S44, so that spatial positions of the mechanical arm model, the TMS coil model, and the 3D camera model are respectively matched with actual spatial positions of the mechanical arm, the TMS coil, and the 3D camera.

Specifically, in step S5, a movement path planning algorithm for a mechanical arm is relatively complicated in general, and since the models, obstacle, and path in this embodiment are all known, a manual path planning method is adopted. A straight path is used at a position far away from the head model (greater than 30 mm), and an arc path is used near the head model (less than/equal to 30 mm), so as to move the TMS coil around the head to a next magnetic stimulation point to be magnetically stimulated. Since 3D data of the head model is known, head model data can be enlarged to leave a safe distance for running, and a shortest arc path between two points on the head model can be calculated.

By automatically navigating movement of a mechanical arm, the present invention avoids influences of human factors on the treatment effect and improves the patient experience.

As still another embodiment of the present invention, the present invention also has a follow-up positioning function. In the process of navigating a mechanical arm, or in the process of face detection, even if the head attitude of a patient changes, real-time follow-up positioning can be performed on the head attitude of the patient by a 3D camera, thereby ensuring the treatment accuracy, and improving the treatment effect and the patient experience.

Specifically, in the process of performing magnetic stimulation treatment on the head of a patient, the smart terminal further performs follow-up positioning on the head of the patient by means of the 3D camera; during the treatment, position information of the head of the patient each time positioning is completed is recorded, and if at a next moment, a distance between positions of the magnetic stimulation point at a current time and a previous time exceeds 5 mm due to movement of the head of the patient, follow-up positioning is started; if the distance does not exceed 5 mm, follow-up positioning is not started; if the head of the patient turns a lot of times, follow-up by the 3D camera and the mechanical arm is suspended, and magnetic stimulation by the TMS coil is also suspended; if the patient is not within an adjustable range of the 3D camera or leaves, the mechanical arm and the magnetic stimulation action of the coil are stopped.

Further, the follow-up positioning includes the steps: fine-tuning the spatial pose of the head model of the patient by the smart terminal, so that the spatial pose of the head model of the patient is matched with the current actual spatial pose of the head of the patient, then repositioning a latest magnetic stimulation point on the head model, finally re-planning a movement path for the mechanical arm, and moving the TMS coil to the latest magnetic stimulation point for treatment.

According to the present invention, video image data of the head of a patient is captured by a camera, the head of the patient is modeled, a facial attitude of the patient is detected and estimated according to modeling data and a captured facial video image to obtain facial attitude data of the patient, then robot navigation is performed according to the facial attitude data to adjust a TMS treatment magnetic stimulation point. Precise positioning of a magnetic stimulation point during each treatment is ensured without the need to wear a light guide ball for positioning, and the problems of TMS positioning and repositioning are solved.

Although the embodiments of the present invention are shown and described, persons of ordinary skill in the art can understand that various changes, modifications, substitutions and transformations can be made to the embodiments without departing from the principle and spirit of the present invention. The scope of the present invention is defined by the appended claims and equivalents thereof.

What is claimed is:

1. A camera-based transcranial magnetic stimulation diagnosis and treatment head modeling system, comprising a 3D scanner, a positioning cap, and a smart terminal, wherein the 3D scanner and the smart terminal are electrically connected, the 3D scanner acquires from different directions 3D image data of a head of a patient wearing the positioning cap and sends acquired 3D image data to the smart terminal;

the smart terminal integrates the 3D image data acquired by the 3D scanner from different directions to obtain a complete 3D point cloud image of the head of the patient, and then obtains complete 3D head model data of the head of the patient through sampling, smoothing, and plane fitting processing; and by using the 3D head model data in combination with MNI brain space coordinates, the smart terminal maps 3D skull data in an MNI space to the 3D head model data of the patient to obtain a 3D head model of the patient.

2. The camera-based transcranial magnetic stimulation diagnosis and treatment head modeling system according to claim 1, wherein, the 3D scanner comprises one 3D camera and one rotating support, the 3D camera is installed on the rotating support, the rotating support is driven to rotate by a motor, and the motor is electrically connected to the smart terminal; and when the 3D image data of the head of the patient is acquired, the smart terminal controls the motor to drive the rotating support to rotate at a uniform speed, so that the 3D camera moves circumferentially around the head of the patient at a uniform speed and acquires the 3D image data of the head of the patient from different directions.

3. The camera-based transcranial magnetic stimulation diagnosis and treatment head modeling system according to claim 2, wherein, the image data captured by the 3D camera comprises a color image, a depth image, and a 3D point cloud image.

4. The camera-based transcranial magnetic stimulation diagnosis and treatment head modeling system according to claim 3, wherein, the positioning cap is a white head cover made of an elastic material, and is configured to cover hair of the patient;

and the positioning cap is provided with a plurality of Mark points to facilitate image data acquisition by the 3D camera.

5. The camera-based transcranial magnetic stimulation diagnosis and treatment head modeling system according to claim 1, wherein, the 3D scanner comprises a plurality of 3D cameras and one fixing support, and the 3D cameras are all installed on the fixing support; and when the 3D image data of the head of the patient is acquired, the smart terminal controls the 3D cameras to simultaneously acquire the 3D image data of the head of the patient from different directions.

6. The camera-based transcranial magnetic stimulation diagnosis and treatment head modeling system according to claim 5, wherein, the image data captured by the 3D camera comprises a color image, a depth image, and a 3D point cloud image.

7. The camera-based transcranial magnetic stimulation diagnosis and treatment head modeling system according to claim 1, wherein, the smart terminal is configured to perform a method for integrating the 3D image data acquired from different directions comprising: calculating, by identifying facial feature points in images acquired from different directions, a matching relationship between the images, then obtaining, through a 3D point cloud ICP algorithm, a spatial position relationship between point cloud images acquired from different directions, and finally, performing rotation and translation operations on all point cloud image data according to the matching relationship and the spatial position relationship to obtain the complete 3D point cloud image of the head of the patient.

* * * * *